United States Patent [19]

Matsutani et al.

[11] Patent Number: 5,417,710
[45] Date of Patent: May 23, 1995

[54] SUTURE GUIDE AND A FIXING MECHANISM OF THE SUTURE GUIDE

[75] Inventors: Kanji Matsutani; Masaaki Matsutani; Yoshimasa Tochimura, all of Tochigi, Japan

[73] Assignee: Kabushiki Kaisha Matsutani Seisakusho, Japan

[21] Appl. No.: 22,477

[22] Filed: Feb. 25, 1993

[30] Foreign Application Priority Data

Feb. 27, 1992 [JP] Japan .................................. 4-075585

[51] Int. Cl.⁶ .................................................. A61B 17/00
[52] U.S. Cl. ................................. 606/224; 29/515; 72/420; 72/422; 72/419
[58] Field of Search ........................ 606/222, 224–226; 223/102; 163/1, 5; 29/748, 753, 861, 862, 882, 515–517; 72/419, 420, 422

[56] References Cited

U.S. PATENT DOCUMENTS

| | | | |
|---|---|---|---|
| 3,710,483 | 1/1973 | Morgan et al. | 29/753 |
| 3,753,280 | 8/1973 | Blakeney et al. | 29/753 |
| 4,335,497 | 6/1982 | Casey | 29/753 |
| 4,505,034 | 3/1985 | Reidt | 29/753 |
| 4,799,311 | 1/1989 | Matsutani . | |
| 5,020,216 | 6/1991 | Ishioka | 29/753 |
| 5,025,549 | 6/1991 | Hornung et al. | 29/753 |

Primary Examiner—Stephen C. Pellegrino
Assistant Examiner—Jeffrey A. Schmidt
Attorney, Agent, or Firm—Townsend & Banta

[57] ABSTRACT

A suture guide used for inserting a suture into a hole of an eyeless needle positioned between an upper guide and a lower guide. This suture guide comprises a first guide member having a certain plane and the second guide member having a first plane positioned lower than the plane of the first guide member and a second plane crossing the first plane, This suture guide also has fixing means combining the first guide member and the second member together to form a guide having a guiding corner with the plane of the first guide member and the second plane of the second member and the guide disposed next to the lower mold to face the guiding corner to the hole of the eyeless needle. A positioning mechanism of a suture guide for inserting a suture into a hole of an eyeless needle positioned between an upper guide and a lower guide is desirable for the suture guide. This mechanism comprises an arm for holding the suture guide via moving member and a swing pin disposed apart from the lower mold and perpendicular to a moving plane of the upper mold. The arm is attached to the swing pin as to swing along a side face of the lower mold to a desirable position.

5 Claims, 4 Drawing Sheets

SUTURE GUIDE AND A FIXING MECHANISM OF THE SUTURE GUIDE

BACKGROUND OF THE INVENTION

This invention relates to a suture guide used when attaching a suture to an eyeless needle for medical use and a fixing mechanism for the suture guide.

DESCRIPTION OF THE PRIOR ART

A medical needle used for stitching an organism is usually an eyeless needle having a sharp point at one end and a hole on an end face of the other end (a root end). This kind of needle has a thickness of 0.14 mm – 1.40 mm and its hole for holding a suture is half the size of the thickness. By inserting the suture to the hole of the needle and by crimping the root end, the suture is attached to the needle.

With the advance of the medical art, a micro needle is required for stitching minute blood vessels and a minute nerve in the fields of brain surgery, eye surgery, finger surgery, and so on. For this reason, a micro needle having a thickness of 23 $\mu$m – 27 $\mu$m has been developed and for this needle, a thin suture having a thickness of 5 $\mu$m has also been developed.

Usually a crimping apparatus for attaching a suture to an eyeless needle has upper and lower molds and a suture guide disposed in front of the molds.

U.S. Pat. No. 4,799,311 to Matshutani discloses an apparatus for attaching a suture to a needle hole. This apparatus has a tapered guide tunnel having a suture exit the same width as the hole of the needle and a wider suture entrance than the suture exit. This apparatus sends a suture to the hole of the needle through the suture tunnel. If the diameter of the suture exit is wider than the hole, it becomes difficult to guide the suture to the hole smoothly. Thus, it is required to form the suture exit to have the same width as the hole and it is also required to make the inner face of the tunnel flat.

The diameter of the hole, which is formed in a needle having a thickness of 23 $\mu$m – 27 $\mu$m, is 10 $\mu$m – 15 $\mu$m. Thus, it is desirable that the guide tunnel have the same width as the hole of the eyeless needle, but it is difficult to form such a small guide tunnel and to make the inner surface flat.

Moreover, because the guide tunnel is a tube, the inside of the guide tunnel is invisible. Thus, the suture deposited inside cannot be seen from the outside and it is difficult to handle the suture to insert it into the hole of the needle.

SUMMARY OF THE INVENTION

The purpose of this invention is to provide a suture guide for guiding a minute suture to the hole of the eyeless needle and to make the suture visible from the outside of the suture guide.

The suture guide of this invention is an apparatus for inserting a suture into a hole of the needle positioned between the upper guide and the lower guide. The apparatus comprises the first guide member having a plane and a second guide member having a first plane which is lower than the top of the first guide member and a second plane which is crossing the first plane. This suture guide also has a fixing means for holding the first guide member and the second member together. By contacting the first plane of the second member to the first plane, a .guide corner for the suture is formed with those planes. The guide section is disposed in front of the hole of the needle.

With this suture guide, even the eyeless needle is very minute and the suture is also very thin, an operator can guide the suture to the eyeless needle. This suture guide also makes the suture visible to the operator, and the operator can confirm whether the suture is inserted into a hole of the eyeless needle.

When the plane of the first guide member contacts the first plane of the second guide member, those two planes make a sharp corner. Thus, by disposing this corner in front of the hole of the micro needle, an end of the suture can be guided toward the hole. As described above, the guiding corner of the suture guide is formed with two planes, the upper part of the guide portion is opened and an operator can see the suture on the guide while handling the suture.

It is desirable to position the side face of the suture guide next to a side face of the lower mold and to form an escape gap for the suture at a side corner which is formed with the second plane and the side face of the second guide member. This escape gap allows the suture connection to the eyeless needle to be shifted when the eyeless needle is crimped.

With this escape gap, injury to the suture can be avoided by crushing the hole with the molds, a connection position of the suture and the eyeless needle shifts downward and the suture can bend into the escape gap to avoid damage.

Another purpose of this invention is to provide a structure for the suture guide described above. The positioning mechanism of this suture guide has an arm for holding the suture guide by a moving member and a pin disposed apart from the lower mold and perpendicular to the moving plane of the upper mold. The arm is attached to the pin to swing along a side face of the lower mold to a desirable position. Thus, with this mechanism the suture guide is positioned at a desirable place surely and easily.

Because the suture guide can pivot at the pin and the suture guide is attached to a moving member, the suture guide can be positioned to any desirable place. This positioning mechanism is useful for changing the position of the suture guide in respect to the thickness of the eyeless needle.

BRIEF DESCRIPTION OF THE DRAWINGS

The accompanying drawings present the preferred embodiments of the present invention, in which.

DESCRIPTION OF THE PREFERRED EMBODIMENTS

This invention provides a suture guide which can accurately guide a thin suture when inserting the suture into a hole of an eyeless needle to be held between upper and lower molds. This suture guide also makes the structure on the suture guide visible from the outside in order to confirm whether the suture is inserted into the hole of the eyeless needle. The positioning structure of the suture guide makes the suture guide move along a side face of the lower mold and it can change the position of the suture guide with respect to a position of the hole of the eyeless needle, where the position of the hole is up to the thickness of the eyeless needle. The mechanism of the crimping apparatus is explained below.

Figure 3:
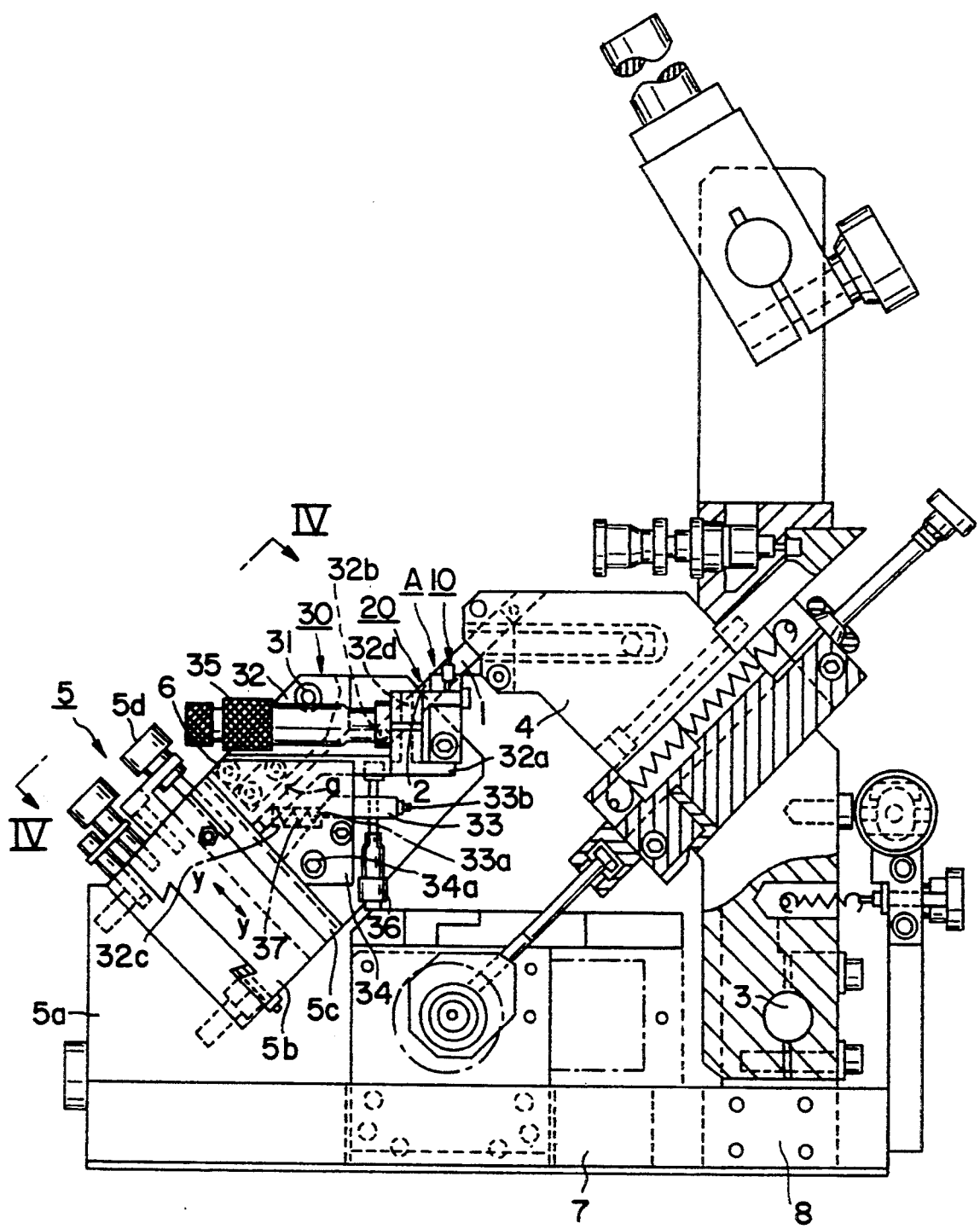
FIG. 3 shows a structure for positioning the suture guide.
Figure 4:
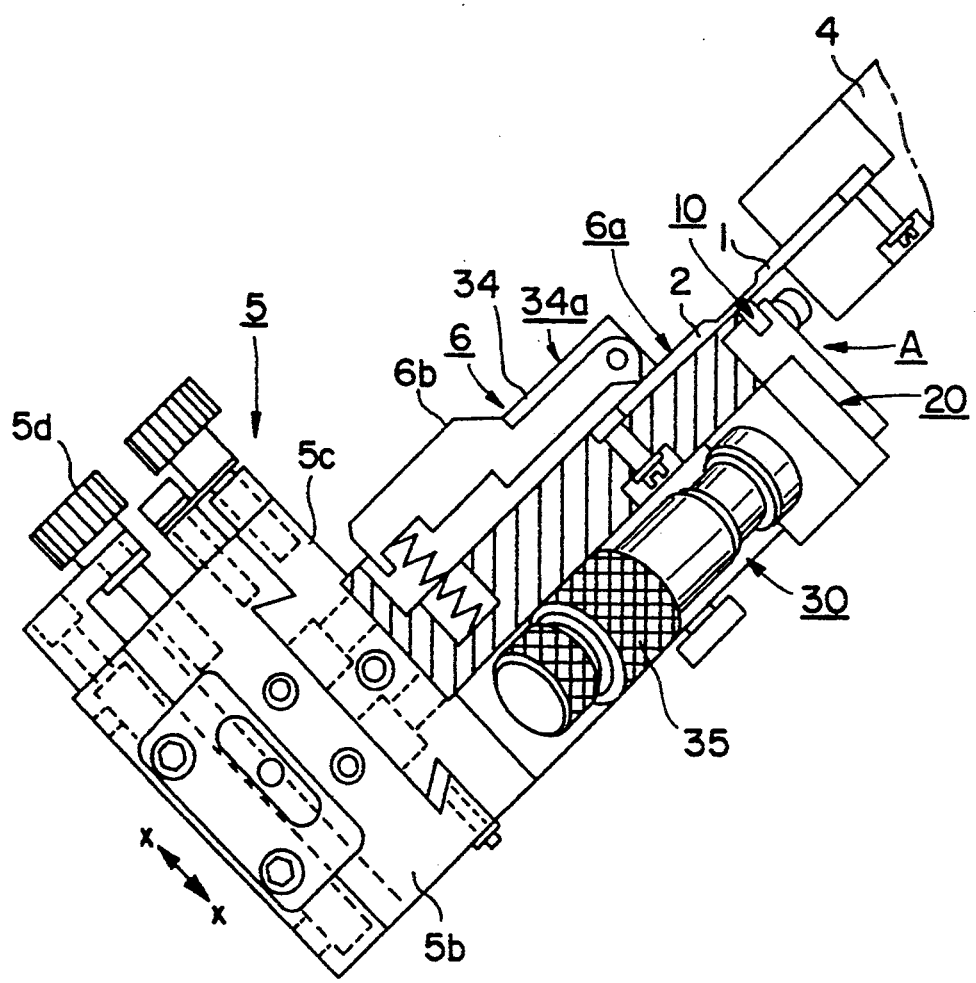
FIG. 4 is a front view showing a structure for positioning the suture guide.

As shown in FIGS. 3 and 4, an upper mold 1 is fixed to a arm 4 which can rotate about a pivoting axis 3. The lower mold 2 is coupled with a lower mold holder 6 on an x-y table. A suture guide A is disposed next to the lower mold 2. The pivoting axis 3 is positioned with a stand 7 on a base frame 8 to be rotation-free. Thus, the upper mold 1 reciprocates on a circular truck.

An x-y table 5 has a mechanism to move the lower mold holder 6 on a plane which is perpendicular to a moving plane of the upper mold 1. Defining a direction parallel with the root end of the needle as a x direction (as shown in FIG. 4), and a direction perpendicular to the root end as a Y direction, this x-y table 5 finely moves the lower mold holder 6 in the two directions. The x-y table 5 comprises a base table 5a, an x table 5b moving in x direction and a y table 5c moving in y direction. This base table 5a is mounted on the base frame 7 and the lower mold 2 is fixed on the upper face of the y table. Thus, by moving the x and y tables 5b and 5c to the x and y directions, it can position the lower mold to an exact place to contact the upper mold 1.

The lower mold holder 6 has a groove 6a and the lower mold 2 disposed in this groove 6a can be fixed with a clamp lever 6b.

The upper mold 1 and the lower holder 2 are disposed from a front side of the crimping apparatus (left hand in FIG. 3) to a back side of the apparatus (right hand in FIG. 3) having a certain angle. The upper mold 1 is disposed to be on a line with the lower mold 2 when they contact each other.

The angle of the upper mold i and lower mold 2 is not limited to one example. This angle is decided for the convenience of an operator sitting in front of the apparatus for inserting the suture into the hole of the eyeless needle, for holding the eyeless needle on the lower mold 2 and for seeing the suture. In this embodiment, the angle is set at 45 degrees.

At the top of the upper mold 1 and lower mold 2, a small groove is formed for holding the micro needle. This groove has the same width as the needle. The micro needle is positioned perpendicular to the upper and lower molds 1 and 2 when the apparatus processes the micro needle.

In this embodiment the operator positions the micro needle on a lower mold 2 and holds the micro needle by clamping it with the upper and lower molds 1 and 2. Then the operator inserts a suture into the hole formed on the root face of the micro needle with the suture guide A. By rotating the arm 4 to crimp the root end of the needle, a suture is attached to the micro needle.

By rotating the arm 4 backward, the upper mold 1 moves apart from the lower mold 2 to make it possible to remove the micro needle from molds 1 and 2 and to insert a new unprocessed micro needle.

Figure 1:
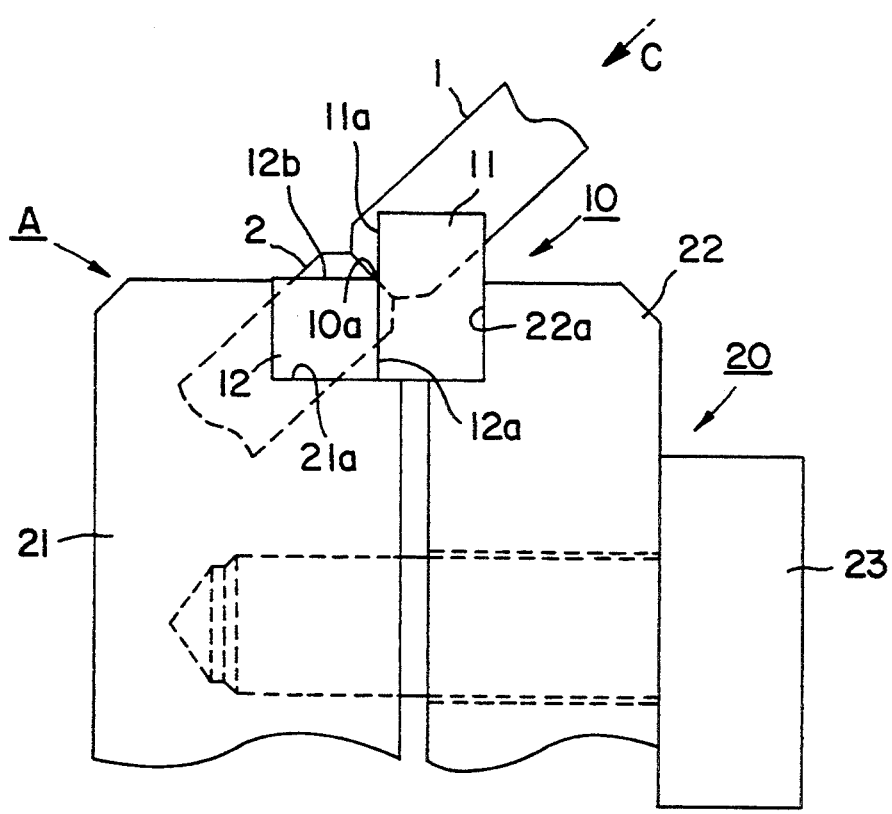
FIG. 1 is a side view showing a relative position of a suture guide and molds.
Figure 2:
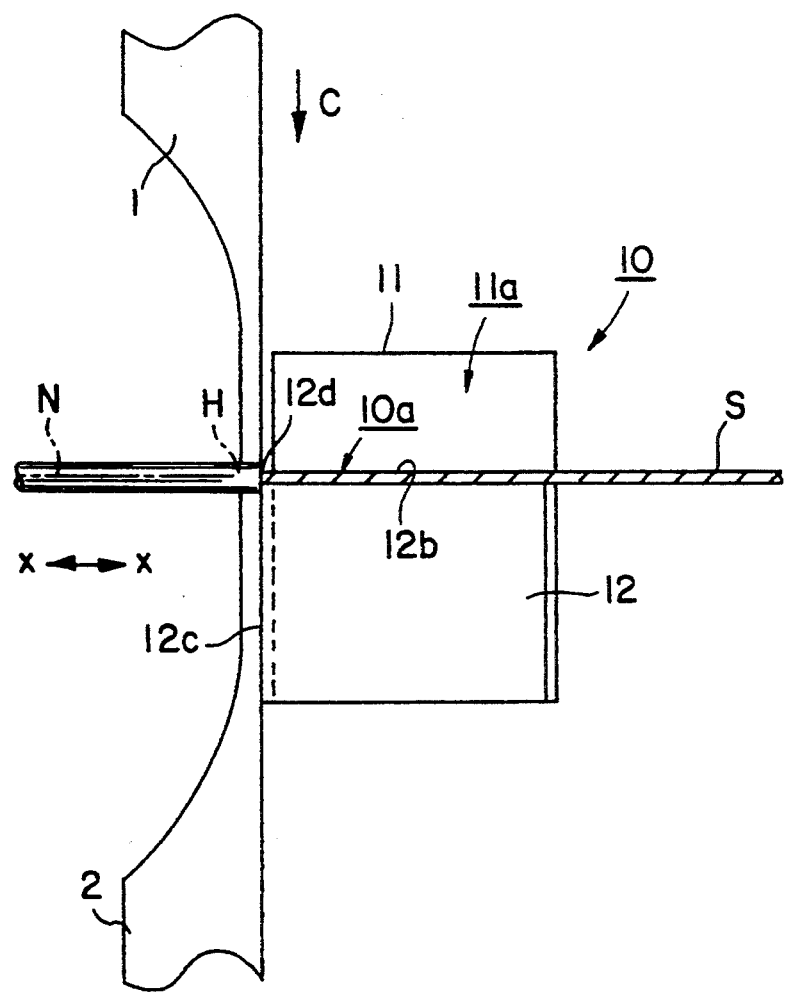
FIG. 2 is a front view of a relative position of a suture guide and molds.

As shown in FIGS. 1-3, the suture guide A comprises a guide 10 disposed next to the lower mold 2, a clamping member 20 for fixing the guide member 10 and an adjusting member 30 for positioning the guide member 10 to a desirable position. This adjusting member 30 is fixed to a certain position of the x-y table 5. By disposing the guide 10 next to a side face of the lower mold 2 and by disposing a guiding corner 10a, which is a corner formed with the plane of the first guide member and the second plane of the second member, to a position facing the hole H of the eyeless needle N, the suture S can be guided along the guiding corner 10A to insert it into the hole H of the eyeless needle N. The adjusting member 30 can move the guide 10 to the desired position.

The guide 10 comprises the first guide member 11 and the second guide member 12.

The first guide member 11 has a height (the length of the guide member 11 in a vertical direction) for facing a side face of the upper mold 1 and at least the plane which forms a guiding corner 10a has a fine flat face formed by polishing.

The second guide member 12 is shorter than the first guide member 11 and its first and second plane 12a and 12b has fine flat faces and a corner formed by planes 12a and 12b which are finished to have a fine straight edge. In this embodiment, the corner has a right angle.

Because the first plane 12a of the second guide member 12 contacts the plane 11a of the first guide member 11 and the third plane 12c perpendicular to the first and second planes 12a, 12b contacts to the side face of the lower mold as well, planes 12a, 12c should be formed to have fine flat faces.

The corner between the second and the third planes 12b, 12c of the second guide member 12 is chipped to be affable to form an inclined plane 12d as an escape gap for the suture.

The clamping member 20 is a device for combining the first guide member 11 and the second guide member 12 to form guide 10. This clamping member 20 comprises a main body 21 and fixing member 22. Main body 21 and fixing member 22 have notches 21a, 22a to hold the guide members 11, 12. By positioning the first guide member 11 in the rear position of the apparatus and the second guide member 12 in the front position of the apparatus, guide members 11, 12 are put in notches 21a, 22a of the clamping member 20. Then by clamping the main body 21 and the fixing member 22 with a screw 23, guide member 11, 12 are combined in one body to form the guiding corner 10a, as well as the guide 10.

The adjusting member 30 is for changing the position of the guide 10. This member 30 is used for adjusting the position of the guiding corner 10a to correspond with the position of the hole H of the eyeless needle N where the molds 1, 2, the thickness of the suture S, or the eyeless needle N are changed.

The adjusting member 30 is fixed to a lower mold holder 6 mounted on the x-y table 5. The adjusting member 30 comprises a supporting arm 32 rotatingly attached to a pin 31, a bracket 33 coupled with the lower mold holder 6 and a pressing plate 34 on the bracket 33 pressing the supporting arm 32.

The rear end of the supporting arm 32 (which is in the front side of the crimping apparatus) is coupled with a U-shaped bracket 32a. At the front of the supporting arm 32) which is the back side of the crimping apparatus) there is a spring receiver 32c.

An adjusting screw 35 is attached to the bracket 32a in a front-rear direction of the apparatus like a regular micrometer. By clamping a slit 32d with the bolt 32b, the adjusting screw 35 is fixed to the bracket 32a. The clamping member 20 is attached to the top of the adjusting screw 35.

The bracket 33 is coupled with a spring receiver 33a at a position facing the spring receiver 32c of the supporting arm 32 and a fixing member 33b disposed in the horizontal direction. This fixing member 33b is coupled with an adjusting member 36 in the vertical direction like a regular micrometer. A spring 37 pressing the supporting arm 32 in an a-arrow direction is disposed between the spring receiver 32c and the other spring receiver 33a.

The bracket 33 is coupled with the elastic pressure plate 34 with a bolt 34a. This pressure plate 34 is a device for keeping the supporting arm 32 at a certain position by pushing a side of the supporting arm 32.

As shown in FIG. 2 and FIG. 3, the guiding corner 10a is formed with the plane 11a of the first guide member 11 and the second plane 12b of the second guide member 12 when the clamping member 20 clamps the guide members 11, 12 together. Because the plane 11a of the first guide member 11 and the second plane 12b of the second guide member 12 have fine flat faces, the guiding corner becomes sharp and no aperture is formed between them.

Regarding the guiding corner 10a, it is impossible to form such a sharp corner by cutting off from a one piece block with a device like an end mill, a milling cutter, or a side cutter, and by polishing the cut face. A crossing line of two planes is usually formed C-shaped or R-shaped face of 0.1 mm width to avoid a concentration of the stress when cutting a face. Thus, even if cutting a block along a line on which the corner is formed to make a sharp edged corner, such a machine damages the sharp edge by the processing stress. Then if the guiding corner has a C-shaped or R-shaped face of 0.1 mm width, a suture having a thickness of 5 μm cannot be easily guided to the hole of the eyeless needle.

This invention solves the problem by forming a guide 10 with two portions, namely the guide members 11 and 12.

The guide 10 is disposed to contact to the side face of the lower mold 2. As shown in FIG. 2, the guide 10 is disposed next to the lower mold 2 as to position the guiding corner 10a for facing the hole H of the micro needle N. The disposing direction of the guiding corner 10 corresponds to the x direction of the x-y table.

The disposing position of the guide 10 is desirable to be the same side of the lower mold 2 as a whip hand of the operator. In this embodiment, the guide 10 is positioned on the right side of the lower mold 2 from the operator who sits down in front of the apparatus.

As described above, the mold 1, 2 is disposed vertically with an angle from the back to the front of the apparatus. The guide 10 is disposed so as plane 11a of the first guide member 11 stands vertically and the second plane 12c of the second guide member 12 stands in a horizontal direction. Thus, the operator, who is sitting in front of the crimping apparatus, clearly sees the guiding corner 10a in order to handle the suture S. The operator can insert the suture S into the hole H of the micro needle N while watching the moving of the suture S.

When making the lower mold 2 contact the guide 10, if the first guide member 11 interferes with the upper mold 1, a frictional resistance between them influences the rotation of the arm 4. Thus, to avoid this bad influence, the guide 10 is disposed so as not to make the first guide member 11 contact the upper mold 1. For this reason, there is a small discrepancy between the guide members 11, 12 when clamping them with the clamping member 20.

After positioning the micro needle N on the guide lower mold 2, the suture S, which is guided along the guiding corner 10a, is inserted into the hole H of the micro needle N. When the hole H of the micro needle N is crimped by pressing with upper mold 1, the hole H of the micro needle N is crushed to shift a connecting position of the suture S below. With this shift of the connecting position, the suture S bends to the inclined plane 12d. Because of this inclined plane 12d, the edge of the second guide member 12 has an obtuse angle to avoid harming the suture S with the edge.

When a thickness of the micro needle N changes, the size of the center of the hole H also changes. Thus, it is necessary to change the relative position of the guide 10 to the lower mold 2. In this invention, the position is easily changed by using an adjustment member 30.

Because the supporting arm 32 is kept in position by pressure of the pressure plate 34, the guide 10 can move along the side face of the lower mold 2 to face the guiding corner 10a to the hole H of the eyeless needle N, by rotating the screw 36, 35 to the desirable position.

The individual components shown in outline or designated by blocks in the drawings are well known in the suture guiding arts of the needle crimping apparatus, and their specific construction and operation are not critical to the operation or best mode for carrying out the invention.

While the present invention has been described with respect to what is presently considered to be the preferred embodiment, it is to be understood that the invention is not limited to the disclosed embodiment. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A suture guide used for inserting a suture into a hole of an eyeless needle held between an upper mold and a lower mold, comprising:
   a first guide member having a planar surface,
   a second guide member having a first planar surface and a second planar surface line contacting with said first planar surface at a guide corner,
   said first guide member being coupled with said second guide member so that said planar surface of said first guide member contacts and is co-planar with said first planar surface of said second guide member, and a part of said planar surface of said first guide member extends above said first planar surface of said second guide member,
   a fixing means for fixing said first guide member and second guide member,
   said suture guide being disposed adjacent a side face of said lower mold so that a hole formed in an end of said eyeless needle which is held between the upper and lower mold faces and is aligned with a guiding corner formed between the planar surface of said first guide and the second planar surface of said second guide,
   said suture guide being completely open above said guide corner so that an operator can view the entire corner while inserting a suture along the guide corner and into said hole of the eyeless needle.

2. A suture guide according to claim 1, wherein a third planar surface of said second guide member, line-contacting said first planar surface of said second guide member, is disposed so as to confront a face of said lower mold.

3. A suture guide according to claim 2, wherein said second guide member has an escape gap at a corner formed with said second planar surface and said third planar surface of said second guide member for allowing a suture to be shifted downward when said hole of said eyeless needle is crushed.

4. A suture guide according to claim 3, wherein said escape gap is formed by an incline planar surface extending between said second planar surface and said third planar surface of said second guide member.

5. A suture guide used for inserting a suture into a hole of an eyeless needle held between an upper mold and a lower mold, comprising:

a first guide member having a planar surface, a second guide member having a first planar surface and a second planar surface line contacting with said first planar surface at a guide corner, said first guide member being coupled with said second guide member so that said planar surface of said first guide member contacts and is co-planar with said first planar surface of said second guide member, and a part of said planar surface of said first guide member extends above said first planar surface of said second guide member, a fixing means for fixing said first guide member and second guide member, said suture guide being disposed adjacent a side face of said lower mold so that a hole formed in an end of said eyeless needle which is held between the upper and lower mold faces and is aligned with a guiding corner formed between the planar surface of said first guide and is aligned with the second planar surface of said second guide, said suture guide being completely open above the guide corner so that an operator can view the entire corner while inserting a suture along the guide corner and into said hole of the eyeless needle, an adjusting member for positioning the guide relative to an eyeless needle held between said upper and lower molds, said adjusting number comprising: a supporting arm for adjusting the position of said first guide member and second guide member, a pin disposed apart from said upper and lower mold, said supporting arm rotatably attached by said pin to a lower mold holder so that said supporting arm can rotate along the side face of said lower mold to move the guide to a desirable position.

* * * * *